(12) United States Patent
Eibl et al.

(10) Patent No.: US 11,511,040 B2
(45) Date of Patent: *Nov. 29, 2022

(54) DYNAMICALLY CONTROLLABLE PATIENT FLUID CONTROL DEVICE

(71) Applicant: 1929803 ONTARIO CORP., Sudbury (CA)

(72) Inventors: Joseph Eibl, Sudbury (CA); Jon-Emile Kenny, Sudbury (CA)

(73) Assignee: 1929803 Ontario Corp., Sudbury (CA)

( * ) Notice: Subject to any disclaimer, the term of this patent is extended or adjusted under 35 U.S.C. 154(b) by 329 days.

This patent is subject to a terminal disclaimer.

(21) Appl. No.: 16/882,209

(22) Filed: May 22, 2020

(65) Prior Publication Data
US 2020/0282143 A1 Sep. 10, 2020

Related U.S. Application Data

(62) Division of application No. 16/297,197, filed on Mar. 8, 2019, now Pat. No. 10,661,009.

(Continued)

(51) Int. Cl.
*A61M 5/172* (2006.01)
*A61M 5/142* (2006.01)
(Continued)

(52) U.S. Cl.
CPC ............. *A61M 5/1723* (2013.01); *A61B 8/06* (2013.01); *A61B 8/488* (2013.01); *A61M 5/142* (2013.01);
(Continued)

(58) Field of Classification Search
CPC .. A61M 2205/3334; A61M 2205/3375; A61M 2205/502; A61M 2230/04;
(Continued)

(56) References Cited

U.S. PATENT DOCUMENTS

| 4,103,679 A | 8/1978 | Aronson |
| 10,394,209 B2 | 8/2019 | Goodon et al. |

(Continued)

FOREIGN PATENT DOCUMENTS

| CA | 2950919 A1 | 1/2016 |
| CN | 102046222 A | 5/2011 |

(Continued)

OTHER PUBLICATIONS

Guillaume, Mahe, et al., "Statement for Doppler waveforms analysis", VASA: Zeitschrift Fuer Gefaesskrankheiten—Journal of Vascular Diseases, vol. 46, No. 5, Aug. 1, 2017 (Aug. 1, 2017), pp. 337-345, XP55848917, DE, ISSN: 0301-1526, DOI: 10.1024/0301-1526/a000638.

*Primary Examiner* — Quynh-Nhu H. Vu
(74) *Attorney, Agent, or Firm* — Perkins Coie LLP

(57) ABSTRACT

A fluid control device includes an interface to a remote fluid monitoring sensor that detects fluid flow in a patient. In some embodiments, a processor within the fluid delivery device is programmed to adjust the delivery or withdrawal of fluids based on the fluid flow signals provided by the sensor. In some embodiments, the fluid control device can display and/or record fluid flow signals thereby acting as a hemodynamic monitor.

11 Claims, 3 Drawing Sheets

Related U.S. Application Data

(60) Provisional application No. 62/640,903, filed on Mar. 9, 2018.

(51) Int. Cl.
   *A61B 8/06* (2006.01)
   *A61B 8/08* (2006.01)

(52) U.S. Cl.
   CPC . *A61M 2205/18* (2013.01); *A61M 2205/3334* (2013.01); *A61M 2205/3375* (2013.01); *A61M 2205/502* (2013.01); *A61M 2230/04* (2013.01)

(58) Field of Classification Search
   CPC .............. A61M 5/142; A61M 5/1723; A61M 2005/1726; A61B 8/06; A61B 8/465; A61B 8/488; A61B 8/5207; A61B 8/5223
   See application file for complete search history.

(56) References Cited

U.S. PATENT DOCUMENTS

| | | | |
|---|---|---|---|
| 10,661,009 B2 * | 5/2020 | Eibl | A61M 5/1723 |
| 2001/0021817 A1 * | 9/2001 | Brugger | A61M 60/546 604/6.11 |
| 2002/0042574 A1 | 4/2002 | Manor et al. | |
| 2005/0156491 A1 | 7/2005 | Scott | |
| 2006/0135940 A1 | 6/2006 | Joshi | |
| 2006/0206032 A1 | 9/2006 | Miele et al. | |
| 2006/0264756 A1 | 11/2006 | Lo et al. | |
| 2008/0208273 A1 | 8/2008 | Owen et al. | |
| 2009/0221948 A1 | 9/2009 | Szamosfalvi et al. | |
| 2010/0016725 A1 | 1/2010 | Thiele | |
| 2010/0049052 A1 | 2/2010 | Sharf et al. | |
| 2010/0076315 A1 | 3/2010 | Erkamp et al. | |
| 2011/0137173 A1 | 6/2011 | Lowe et al. | |
| 2012/0138533 A1 * | 6/2012 | Curtis | A61M 1/16 210/85 |
| 2012/0184854 A1 | 7/2012 | Raju et al. | |
| 2012/0277640 A1 | 11/2012 | Lewis, Jr. et al. | |
| 2012/0296216 A1 | 11/2012 | Sharf et al. | |
| 2014/0081144 A1 | 3/2014 | Moehring et al. | |
| 2014/0371594 A1 | 12/2014 | Flynn et al. | |
| 2015/0009782 A1 | 1/2015 | Engl et al. | |
| 2015/0135840 A1 | 5/2015 | Sato et al. | |
| 2015/0289838 A1 | 10/2015 | Nichol et al. | |
| 2015/0335820 A1 | 11/2015 | De Armond et al. | |
| 2016/0206292 A1 | 7/2016 | Vezina | |
| 2017/0080255 A1 | 3/2017 | Law et al. | |
| 2017/0293277 A1 | 10/2017 | Goodon et al. | |
| 2017/0325328 A1 | 11/2017 | Isaac et al. | |
| 2018/0020982 A1 | 1/2018 | Elsherbini et al. | |
| 2018/0206819 A1 | 7/2018 | Saarinen et al. | |
| 2018/0353157 A1 * | 12/2018 | Eibl | A61B 8/5246 |
| 2019/0021659 A1 | 1/2019 | Sajwan et al. | |
| 2019/0059848 A1 | 2/2019 | Owen et al. | |

FOREIGN PATENT DOCUMENTS

| | | |
|---|---|---|
| CN | 102871645 A | 1/2013 |
| CN | 104883967 A | 9/2015 |
| WO | WO2008042559 A2 | 4/2008 |
| WO | WO2009154298 A1 | 12/2009 |
| WO | WO2015074015 A1 | 5/2015 |
| WO | WO2015181167 A1 | 12/2015 |
| WO | WO2017096487 A1 | 6/2017 |

* cited by examiner

DYNAMICALLY CONTROLLABLE PATIENT FLUID CONTROL DEVICE

CROSS-REFERENCE TO RELATED APPLICATION(S)

The present application is a divisional of U.S. patent application Ser. No. 16/297,197, filed Mar. 8, 2019, and claims the benefit of, and priority to, U.S. Provisional Patent Application No. 62/640,903 filed Mar. 9, 2018, both of which applications are herein incorporated by reference in their entireties.

TECHNICAL FIELD

The disclosed technology relates to medical fluid control devices.

SUMMARY

As will be discussed in further detail below, one embodiment of the disclosed technology relates to a patient fluid control device that is configured to receive signals (e.g., Doppler velocimetry, or other signals derived from an echocardiography interrogation of a vessel) from a sensor that detects fluid flow (e.g. blood flow) in one or more of a patient's vessels. The fluid control device includes one or more processors that are programmed to analyze the fluid flow measurements and adjust the delivery of fluids based on the detected fluid flow.

In another embodiment, the disclosed technology relates to a fluid control device that removes or recirculates fluid from a patient such as a dialysis machine. The device is configured to receive signals from a sensor that detects fluid flow in one or more of a patient's vessels in a static or dynamic (i.e., repeated) manner over the course of a clinical intervention. The device includes a processor that is programmed to adjust the removal of fluid from the patient based on the signals received from the sensor.

In some embodiments, a processor is programmed to compare one or more measurements of fluid flow versus an event that should change the fluid flow. Such an event can be the delivery or withdrawal of fluid from the patient or a physical intervention such as a leg raise, ventilator-delivered breath or the like. Signals from the flow sensor are analyzed by the processor for changes in fluid flow measured before and after the event. The processor is programmed to alert the clinician and/or adjust the delivery or withdrawal of fluid from the patient based in part on the signal analysis.

In some embodiments, the fluid control device delivers fluids such as an intravenous fluid pump, and in other embodiments, the fluid control device withdraws or recirculates fluids such as a dialysis machine. The term "fluid control device" is therefore intended to refer to any programmable device that is connectable to a flow sensor and that delivers or withdraws fluids from a patient. The devices are connected via a wired or wireless communication link to a fluid flow sensor that monitors fluid flow (e.g. blood flow) through one or more vessels. In some embodiments, the sensor is an ultrasound patch sensor that directs ultrasound signals into the patient and detects a Doppler shift in the return signals detected by the sensor.

DETAILED DESCRIPTION

Figure 1:
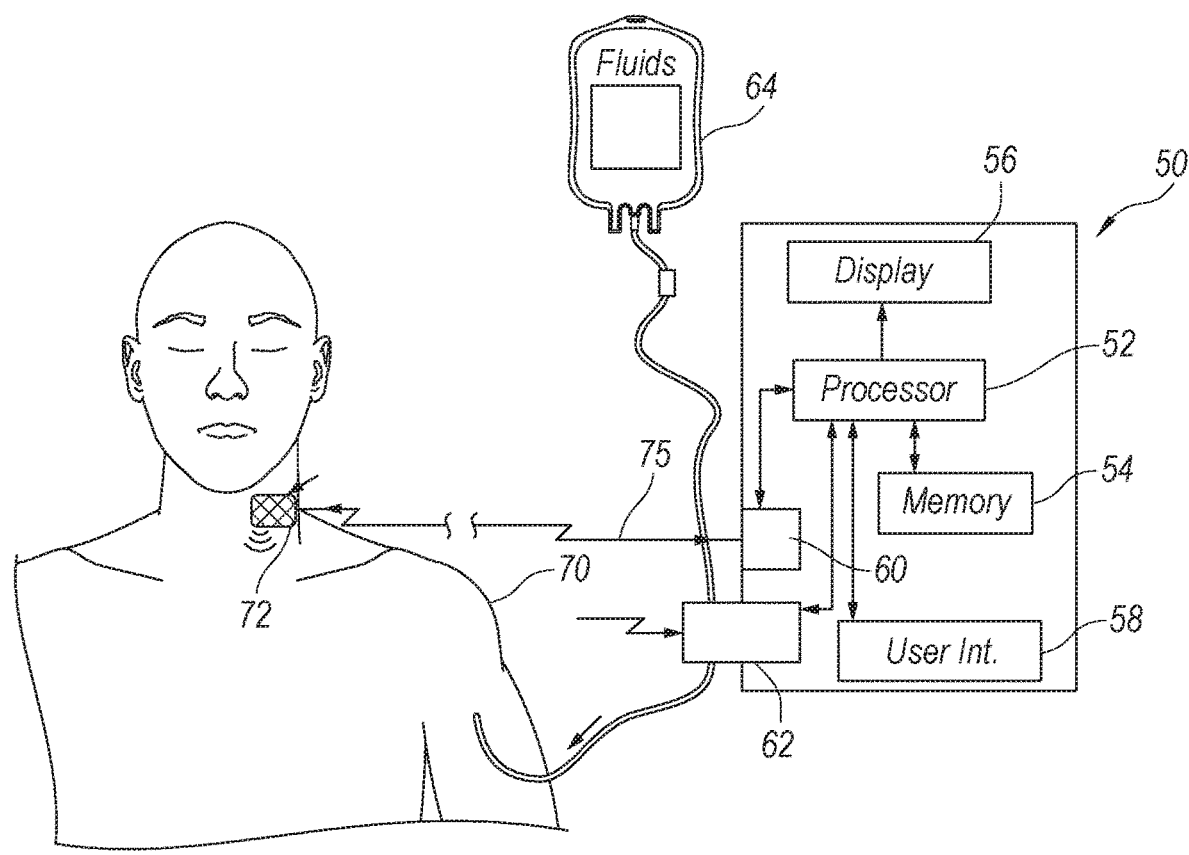
FIG. 1 is a block diagram of a fluid delivery device in accordance with some embodiments of the disclosed technology.

FIG. 1 is a block diagram of a system for controlling a fluid control device in accordance with some embodiments of the disclosed technology. In some embodiments, the fluid control device is designed to deliver fluids to a patient such as a programmable intravenous pump. In other embodiments, the fluid control device is designed to withdraw or withdraw and replace fluids from a patient such as a dialysis machine. In the embodiment shown, a fluid delivery device 50 includes a processor 52 that is configured to execute programmed instructions stored in a memory 54. A display 56 provides visual information to an operator regarding one or more of a rate at which fluids are to be delivered to the patient, the amount of fluid delivered, the time left until fluid delivery is complete etc. A user interface 58 such as a number of buttons, a keyboard or a touch sensitive screen on the display 56 allows an operator to turn the machine on/off, enter patient data, change the rate of delivery, program a bolus delivery of fluid, program a start or stop time etc. A fluid pump 62 is controllable by the processor 52 to deliver precise quantities of a fluid 64 to a patient 70 at a known rate.

In conventional fluid delivery devices, programmed quantities of fluids are delivered at a programmed rate without feedback from the patient 70 regarding how the fluids are being received. A fluid delivery device 50 according to the disclosed technology includes an interface/communication port 60 that receives signals from a flow sensor 72 that monitors fluid flow or other vessel parameters in the patient 70. In one embodiment, the flow sensor 72 detects Doppler signals from one or more vessels in the patient and returns the Doppler signals and/or measurements of the detected flow via a wired (e.g. USB, twisted pair, fiber optic, co-axial cable etc.) or wireless (Bluetooth, Bluetooth LE, Wi-Fi, Zigbee, IR etc.) communication link 75 and are received at the interface 60. Communication signals received at the interface 60 are provided to the processor 52. In some embodiments, the interface/communication port 60 is a physical port into which a corresponding USB plug, twisted pair of cables, co-axial cable or the like is inserted in order to connect the fluid delivery device to the flow sensor 72. In other embodiments, the interface/communication port 60 is an antenna and communication circuitry or an IR receiver etc. that converts wireless signals into electronic signals that can be processed by the processor 52.

The signals from the flow sensor 72 are received by the fluid delivery device 50 and used to adjust the delivery of fluids to the patient 70. In one embodiment, the flow sensor 72 is a pulsed or continuous wave ultrasound device having at least one transmit element and at least element that acts as a receive element. In case of pulsed ultrasound, the transmit element and the receive element may be the same. Ultrasound signals are periodically or continuously transmitted towards a vessel and the reflected ultrasound signals are detected and processed in order to detect the Doppler shift due to blood flowing towards or away from the sensor 72.

If the communication link 75 has sufficient bandwidth, raw ultrasound data signals can be transmitted to the fluid delivery device 50 to be processed off the flow sensor 72. However, in most embodiments, signal processing circuitry and a processor or microcontroller (not shown) within the sensor 72 detect the Doppler signals and a produce a digitized version of the Doppler signals and measurements obtained therefrom for transmission via the wired or wireless communication link 75 to the fluid delivery device 50. In some embodiments, one suitable flow sensor 72 is described in U.S. patent application Ser. No. 15/877,251 filed Jan. 22, 2018 and published as U.S. Patent Publication No. US 2018-0353157 A1, which is herein incorporated by reference in its entirety. In some embodiments, the flow sensor samples the forward and reverse flow Doppler signals to determine their peak values and the centroid frequency/velocity at each sample point. This information is transmitted wirelessly to the flow control device to allow the flow control device to reproduce the Doppler waveforms and calculate metrics from the Doppler information such as Doppler power, VTI (velocity time integral), systolic flow time, etc.

In the embodiment described, the flow sensor 72 is a stand-alone device that processes the received ultrasound data to determine the Doppler shifts and communicates with the fluid delivery device 50 via the communication link 75. In other embodiments, some signal processing components of the flow sensor 72 may be incorporated into the fluid delivery device 50 and the flow sensor 72 includes the ultrasound transmit and receive elements but not all the signal processing components. The fluid delivery device includes some signal processing components necessary to receive either an analog or digitized version of the reflected ultrasound signals and determine the Doppler shifts and compute the metrics therefrom.

As will be appreciated by those skilled in the art, the fluid delivery device 50 also includes additional components besides those shown in FIG. 1, which are omitted to avoid obscuring aspects of disclosed technology. For example, the fluid delivery device generally includes a power supply and communication circuitry to send signals and/or alarms to hospital patient monitoring systems.

Doppler signals and/or measurements computed therefrom are received by the fluid delivery device 50 at the interface 60 and relayed to the processor 52 of the fluid delivery device that is programmed to start/stop/alter the delivery of fluids based on the information received from the flow sensor 72. In some embodiments, the flow sensor 72 detects other measurements besides the Doppler shift of blood flowing in the vessels. Vessel sizes can also be detected from returned ultrasound data. When combined with Doppler signals flowing towards or away from the sensor, estimates of the sizes of different vessels such as the carotid artery versus the jugular vein can be determined and transmitted to the fluid delivery device 50.

In some embodiments, the processor or logic circuitry in the fluid delivery device 50 is configured to perform one or more of auto-titration of administered intravenous fluids, delivery vasoactive medications, to perform dialysis and/or to produce fluid/medication induced warning signs. The device 50 receives real-time arterial and venous Doppler waveforms from a patient (via the flow sensor 72 described above or other Doppler-based input). As its output, the device can provide an indication to an operator to adjust, or can auto-adjust, one or more of: the infusion rate and volume of intravenous fluids as well as the dose and concentration of vasoactive medications. The fluid delivery device 50 can also provide a warning alarm if vital signals indicate a medication/fluid may be causing a problem for the patient (e.g., opioids decreasing respiratory rate, fluids inducing atrial fibrillation etc.).

Intravenous Fluids and Dialysis

In some embodiments, the fluid delivery device 50 is configured to adjust the rate and volume of intravenous fluid based on a quantitative and/or qualitative change in an arterial and/or venous Doppler waveform. The device 50 may also have a warning system/alarm for clinicians prior to making any change in fluid infusion. The venous and arterial Doppler waveforms may be obtained from the external flow sensor 72 or an internal non-invasive or invasive Doppler detection device.

Methods for assessing fluid responsiveness of the heart from an arterial waveform include detecting a change in one or more of: peak systolic velocity, mean velocity, velocity time integral, systolic flow time, end diastolic velocity, absolute flow, Doppler power, and velocity-power combinations. The absence of change, or a decrease, in one or more of the aforementioned variables in response to a fluid infusion/bolus or other provocative maneuver such as a passive leg raise, change in intra-thoracic pressure, or dialysis can warn the clinician and/or slow or cease infusion of intravenous fluid (or dialysis of fluids) automatically is so programmed. The fluid delivery device 50 may also have auto-programmed protocols which infuse a known volume of intravenous fluid and assess the change in the aforementioned arterial Doppler parameters. From this data, fluid infusion or dialysis can be increased, slowed or ceased as so programmed by the clinician.

Figure 2:
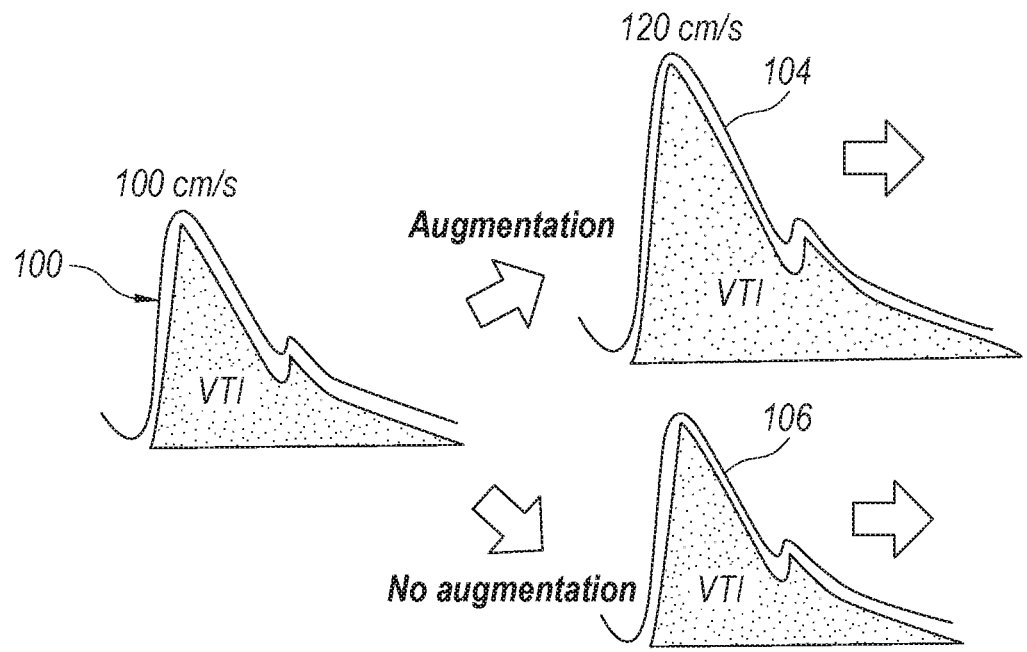
FIG. 2 illustrates two possible changes occurring in a patient's computed velocity time integral (VTI) after a partial delivery of a fluid bolus.

FIG. 2 depicts simple input-measurement-output for the fluid delivery device 50. Note that the intervention is not limited to a fluid challenge but, as above, could also rely upon a leg raise or changes in arterial Doppler based on respiratory variation amongst other stresses placed upon the heart. This process may be iterative. In the embodiment shown, a clinician programs the fluid delivery device 50 to administer a 1000 ml. fluid bolus. Instead of delivering the entire bolus at one time, the device 50 is programmed to deliver a partial bolus and compare the fluid flow measurements pre and post administration. In the example shown, the pre-bolus maximum fluid velocity 100 is 100 cm/s. The system administers a partial 250 ml. bolus and the post bolus Doppler measurements are obtained for comparison. A 100 to 120 cm/s velocity increase 104 represents a 20% increase in peak systolic velocity [PSV]; the y-axis is Doppler velocity; the shaded area is the VTI or velocity time integral for the Doppler pulse. In the embodiment shown, an increase in the PSV is detected and the processor 52 of the fluid delivery device 50 is programmed to deliver the 750 ml. remainder of the bolus. On the other hand, if no increase 106 in the PSV is detected, the processor 52 of the fluid delivery device 50 can operate to hold the remainder of the bolus and set an alarm for an operator.

In some embodiments, the processor of the fluid delivery device stores the pre and post bolus Doppler waveforms in a memory for inclusion into a patient record or for other purposes.

Methods for assessing fluid responsiveness of the heart from an arterial waveform also include detecting a change in the morphology of the arterial waveform, for example a Doppler flow time. As described below, changes in waveform morphology in response to vaso-active infusion can be integrated with on-going assessment of fluid responsiveness following auto-titration of vaso-active medication.

Methods for warning the clinician and/or slowing or ceasing the infusion of intravenous fluid from a venous waveform may include the qualitative or quantitative analysis of the venous velocity morphology as a marker of central venous pressure [i.e. CVP]. The venous waveform can also include relating the diameter of the carotid artery to the diameter of the jugular vein as a marker of CVP or by relating surrogates for arterial and jugular diameter as an indication of central venous pressure. The fluid delivery device 50 may also execute auto-programmed protocols that infuse a known volume of intravenous fluid and assess the change in the aforementioned venous Doppler parameters. From this data, fluid infusion can be increased, slowed or ceased as so programmed by the clinician.

Figure 3:
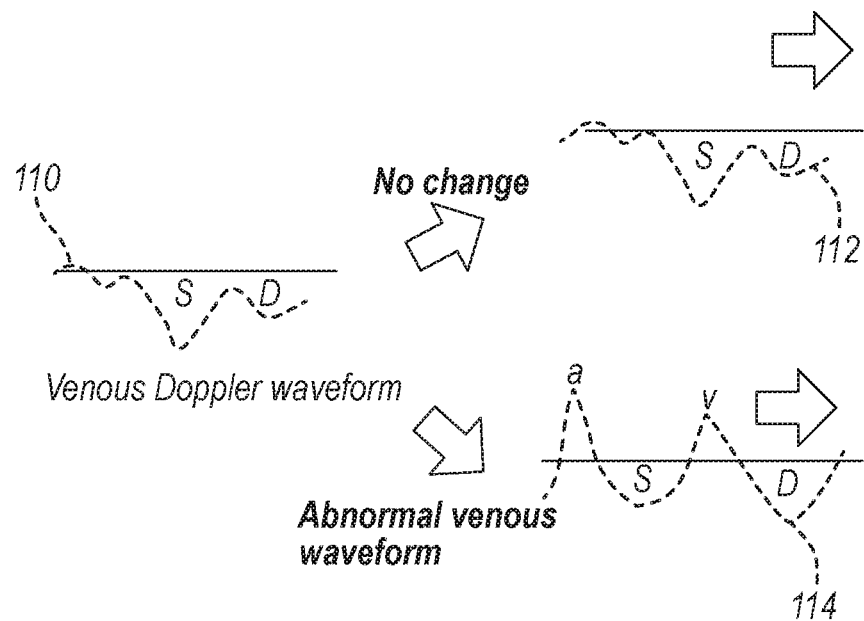
FIG. 3 illustrates two possible changes occurring in a patient's venous Doppler signal after a partial delivery of a fluid bolus.

FIG. 3 depicts a similar iterative process to FIG. 2, but instead, a qualitative analysis of the venous Doppler waveform is utilized. Wave 110 represents the pre-challenge venous Doppler waveform, while waves 112 and 114 represent possible post-challenge Doppler waveforms. Note that the provocation need not be a fluid challenge such as a bolus delivery but could include a provocative maneuver such as a change in intra-thoracic pressure, ventilator-delivered breath, body position or dialysis. Further, the analysis could include quantitative assessment of venous Doppler waveform or other ultrasound-based assessments of the central venous pressure. As shown in FIG. 3, S is systolic venous wave, D is diastolic venous wave, a and v are A and V waves, respectively, which are well-known waves in the CVP—the A wave is the first positive deflection and is the result of the atrial kick while the V wave is the second positive deflection—it's peak marks ventricular filling.

In the example shown, a clinician orders a 1000 ml bolus to be given and the fluid delivery system delivers a partial bolus of 250 ml. Doppler venous signals obtained before and after the fluid challenge are obtained and compared. If little or no changes to the venous Doppler waveform 110 occur, then the fluid delivery device continues to deliver the rest of the 1000 ml. bolus. On the other hand, evolving (e.g. increasing) A and V waves with a reversed S/D ratio (shown in waveform 114) (e.g. the peak diastolic speed now exceeds the peak systolic speed) is highly suggestive of high right heart pressure. In one embodiment, the fluid delivery system suspends the delivery of the remainder of the bolus and/or alerts a clinician. This is but one example of venous Doppler analysis.

If a non-fluid challenge is used, the fluid control device can be programmed to produce an instruction on its display or an audible command telling an operator to perform a leg raise etc. In this way, the fluid control device can look for changes in the Doppler signals after the instruction is given. In other embodiments, the fluid control device can receive signals from a ventilator or other medical device indicating when a therapy is given in order to mark the time to begin looking for changes in the Doppler signals from the remote sensor.

Vaso-Active Medications

As different states of shock result from different pathologies of the heart and/or vasculature, the correction of shock requires specific selection and titration of vaso-active medication(s). The subtype of shock may be inferred from a pattern of arterial and/or venous Doppler waveform analysis. Therefore, vaso-active selection and titration may be based on device analysis of Doppler inputs. Consider the example of a shocked patient with a waveform profile as shown in FIG. 4.

Figure 4:
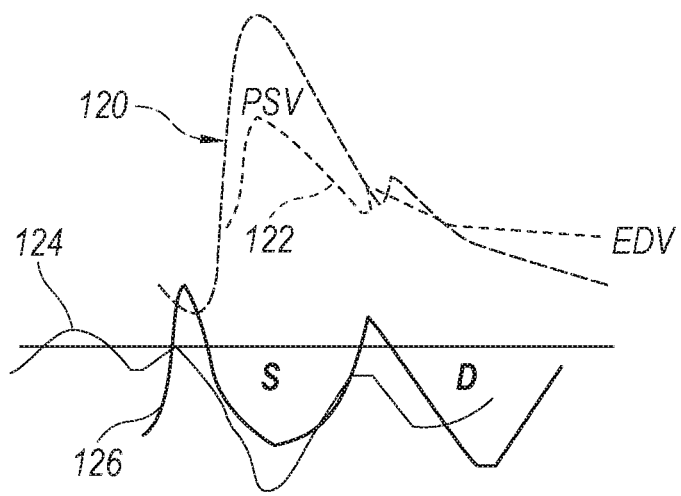
FIG. 4 illustrates possible changes to a peak systolic velocity and an end diastolic velocity and changes of systolic versus diastolic velocity that are simultaneously measured and used to adjust the delivery of a therapy in accordance with some embodiments of the disclosed technology.

FIG. 4 illustrates a hypothetical analysis of simultaneous arterial and venous waveform velocimetry as inputs for an infusion device to make automated changes in intravenous fluids and/or vasoactive medications. Normal arterial and venous Doppler waveforms 120, 124 are included for comparison [shown in dotted lines]. This is one example of many potential analyses in the shocked patient.

The arterial Doppler waveform 122 reveals a lower velocity time integral—suggesting low stroke volume. This is accompanied by a very high end-diastolic arterial Doppler velocity (EDV)—suggesting low peripheral arterial resistance. If simultaneous venous Doppler analysis strongly suggests a high central venous pressure (e.g. waveform 126)—CVP (such as indicated by an increase in the diastolic venous velocity compared with the systolic venous velocity), it is likely that there is simultaneous cardiac dysfunction based on Guytonian physiology. Thus, fluids would be warned against, slowed or ceased and the fluid delivery device can be programmed to suggest a vasoactive medication that increases both cardiac output and peripheral vascular resistance or the infusion dose increased [e.g. epinephrine or to a lesser extent nor-epinephrine]. In this state, a vasoactive medication that increases cardiac function and further lowers peripheral vascular resistance [e.g. dobutamine] would be warned against or down-titrated through the fluid delivery device infusion pump. A similar analysis can be made for other types of general shock such as hypovolemic, cardiogenic, obstructive and distributive and mixed types.

Changes in vaso-active medications may be suggested by the device or automatically executed based on programmed protocols.

Although the disclosed technology is primarily described with respect to a fluid delivery device such as an intravenous fluid pump, the technology is equally useful with other types of fluid management systems such as dialysis machines. In this embodiment, the device includes an interface or communication port where Doppler signals (or un-processed ultrasound echo data) are received from a remote sensor and can be processed and measured by a processor prior to and after the removal of blood for filtering. Doppler signals or other ultrasound measurements are received from a fluid flow sensor and are analyzed by a processor in the device to halt/continue or adjust the rate of fluid withdrawal and replacement.

By including an interface to receive fluid flow measurements from a sensor attached to the patient, the fluid delivery/management device 50 become in effect a hemodynamic monitor that can monitor blood flow over periods of time. Blood flow can be recorded and upper and or lower limits can be set to produce alerts should the limits be exceeded. In some embodiments, the fluid delivery/control device records Doppler waveforms during the course of a longer procedure (e.g., dialysis or other) where multiple readings of the Doppler waveforms are plotted against each other to identify changes over time.

Figure 5:
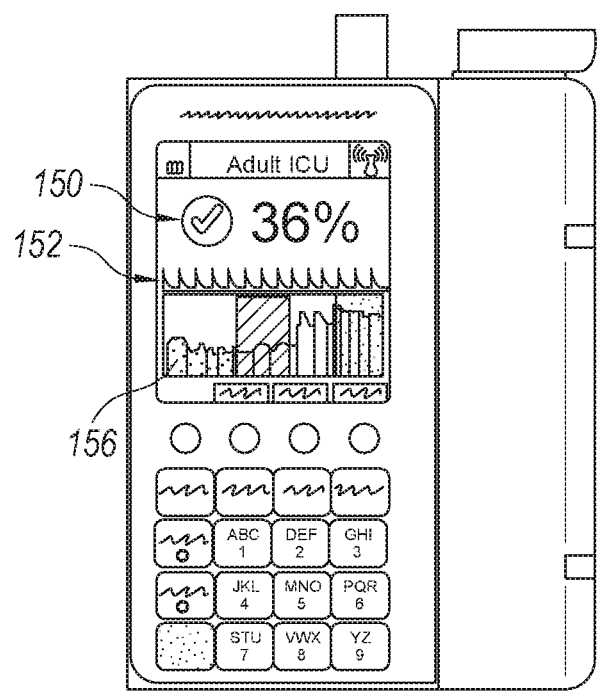
FIG. 5 illustrates a representative user interface (UI) on a fluid control device that shows fluid flow measurements obtained by a remote fluid flow sensor.

FIG. 5 shows an exemplary user interface (UI) on an infusion pump where Doppler waveforms over a number of cardiac cycles are shown on a display. In the embodiment shown, the UI displays (% change post/pre-fluid challenge) 150, the general Doppler waveform 152 and histograms 156 showing a beat by beat quantification of a Doppler waveform parameter. Note this UI could be toggled to zoom/focus on different data visualizations (e.g., just the arterial waveform, just the venous waveform etc.), and time averaged sampling for post/pre-analysis is also enabled. The UI is intended to allow the infusion pump to also function as a hemodynamic monitor.

Measurements from the Doppler waveform such as VTI or peak or centroid velocities can be calculated and displayed. Similarly, such measurements can be averaged and displayed over a number of cardiac cycles. A clinician can perform some fluid challenge and can view how the challenge affects the detected vascular flow.

In some embodiments, an intravenous pump/monitor, dialysis machine or a bedside ultrasound machine receives a measured "calibrated" left ventricular stroke volume (measured invasively or non-invasively) and includes a processor that is programmed to fit the measured left ventricular stroke volume to simultaneously-obtained carotid Doppler tracings from a flow sensor attached to the patient. The calibration of the measured left ventricular stroke volume may be made to fit the carotid velocity, power, velocity-power and/or metrics derived from the Doppler signals produced by the flow sensor. Thereafter, real-time changes in left ventricular stroke volume can be tracked by extrapolation from changes in the carotid Doppler signals.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, SSDs, on-chip non-volatile memory or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a programmed microcontroller, a computer, a system on a chip, or multiple ones, or combinations, of the foregoing. The apparatus can include special purpose logic circuitry, e.g., an FPGA (field programmable gate array) or an ASIC (application-specific integrated circuit).

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code).

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, a programmed microcontroller, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., solid state drives SSDs, magnetic, magneto-optical disks, or optical disks. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can include a display device, e.g., an LCD (liquid crystal display), LED (light emitting diode), or OLED (organic light emitting diode) monitor, for displaying information to the user and a keyboard and a pointing device, such as a touch screen that can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. The biosensor or pump may also be configured to push information to cellular devices, mobile networks or smart devices (e.g., glasses and/or watch).

From the foregoing, it will be appreciated that specific embodiments of the invention have been described herein for purposes of illustration, but that various modifications may be made without deviating from the and scope of the invention. For example, although the embodiments described are for fluid control devices for use on humans, the disclosed technology could also be used with veterinary fluid control devices. Accordingly, the invention is not limited except as by the appended claims.

We claim:

1. A fluid delivery device, comprising:
   a processor programmed to execute a number of instructions;
   a fluid delivery pump that is configured to deliver fluid to a patient, wherein the fluid delivery pump is under control of the processor; and a communication port that is configured to receive fluid flow signals from a remotely located flow sensor;

wherein the instructions cause the processor to control the fluid delivery pump in accordance with the fluid flow signals received from the remotely located flow sensor; and wherein the processor is programmed to compare the fluid flow signals received prior to and after a challenge designed to change the blood flow in a patient and to control the pump based on the comparison.

2. The fluid delivery device of claim 1, further comprising a display that is configured to display the fluid flow signals received from the remotely located fluid flow sensor.

3. The fluid delivery device of claim 2 wherein the display is used to display a graph of peak Doppler velocity of fluid flow in a patient's vessel over time.

4. The fluid delivery device of claim 1, wherein the instructions cause the processor to:

receive an instruction to deliver a bolus of fluid to the patient;

receive signals indicative of a fluid flow in the patient before delivering the bolus;

deliver a portion of the bolus to the patient;

receive signals indicative of the fluid flow in the patient after the portion of the bolus has been delivered;

compare the signals indicative of fluid flow before and after the portion of the bolus was delivered; and deliver a remainder of the bolus based on the comparison.

5. The fluid delivery device of claim 1, where the fluid flow signals received are Doppler signals.

6. The fluid delivery device of claim 5, wherein the Doppler signals are derived from arterial and venous blood flow in vessels of the patient.

7. The fluid delivery device of claim 1 wherein communication port is configured to receive wireless communications indicative of fluid flow in the patient from the remotely located flow sensor.

8. The fluid delivery device of claim 1, further comprising a memory for storing the flow signals.

9. The fluid delivery device of claim 1 wherein the processor is programmed to deliver a bolus of liquid to the patient as a challenge.

10. The fluid delivery device of claim 1 wherein the processor is programmed to generate an instruction to an operator to administer the challenge to the patient.

11. The fluid delivery device of claim 1 wherein the processor is programmed to generate an alarm based on the comparison.

* * * * *